United States Patent [19]

Myers et al.

[11] Patent Number: 4,956,406
[45] Date of Patent: Sep. 11, 1990

[54] BIS-CYCLIC PHOSPHITE COMPOUNDS AND POLYMERIC MATERIALS STABILIZED THEREWITH

[75] Inventors: Garry L. Myers; Richard H. S. Wang, both of Kingsport, Tenn.

[73] Assignee: Eastman Kodak Company, Rochester, N.Y.

[21] Appl. No.: 389,240

[22] Filed: Aug. 3, 1989

[51] Int. Cl.$^5$ .................. C08K 5/524; C08K 5/526
[52] U.S. Cl. .................................. 524/119; 558/78; 252/400.24
[58] Field of Search .................. 524/119; 558/78; 252/400.24

[56] References Cited

U.S. PATENT DOCUMENTS

| | | | |
|---|---|---|---|
| 3,441,633 | 4/1969 | Friedman | 558/78 |
| 3,467,733 | 9/1969 | Dever et al. | 558/78 |
| 3,488,407 | 1/1970 | Schall et al. | 558/78 |
| 3,592,858 | 7/1971 | Brimer | 568/580 |
| 3,714,302 | 1/1973 | Dever et al. | 558/85 |
| 4,141,903 | 2/1979 | Adler | 548/260 |
| 4,219,480 | 8/1980 | White et al. | 548/260 |
| 4,252,750 | 2/1981 | Buysch | 558/78 |
| 4,268,459 | 5/1981 | Hoffman | 524/119 |
| 4,275,004 | 6/1981 | Winter et al. | 534/581 |
| 4,388,431 | 6/1983 | Mauric et al. | 524/119 |
| 4,673,701 | 6/1987 | Minagawa | 524/99 |
| 4,888,371 | 12/1989 | Tajima et al. | 558/78 |

FOREIGN PATENT DOCUMENTS 2223290 10/1987 Japan .................................. 558/78

Primary Examiner—Kriellion Morgan
Attorney, Agent, or Firm—J. Frederick Thomsen; William P. Heath, Jr.

[57] ABSTRACT

Disclosed are novel bis-cyclic phosphite compounds having the formula

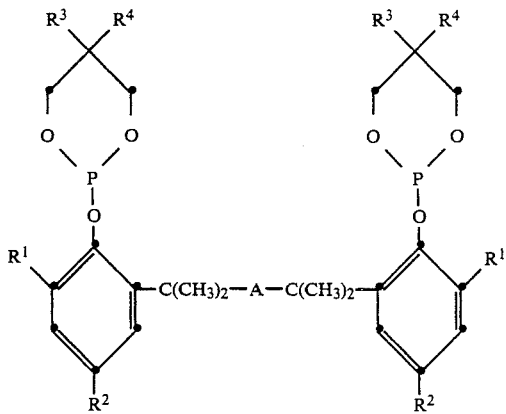

wherein
each $R^1$ is independently selected from hydrogen, alkyl, aralkyl, aryl, carboxy, alkoxycarbonyl or halogen;
each $R^2$ is independently selected from hydrogen, alkyl, aralkyl, alkoxy, aryl, carboxyl, alkoxycarbonyl or halogen;
each $R^3$ and $R^4$ is alkyl; and
A is 1,3- or 1,4-phenylene.

Also disclosed are synthetic polymeric materials stabilized with one or more of the above compounds.

12 Claims, No Drawings

BIS-CYCLIC PHOSPHITE COMPOUNDS AND POLYMERIC MATERIALS STABILIZED THEREWITH

This invention concerns certain novel bis-cyclic phosphite compounds and polymeric materials stabilized therewith. More specifically, this invention concerns certain bis-dioxaphosphorinane compounds containing the residue of a bis(hydroxyphenylpropyl)benzene compound and polymeric materials stabilized against thermally-induced oxidative degradation by the presence therein of at least one of the bis-dioxaphosphorinane compounds.

Synthetic polymeric materials such as polyamides and polyolefins, particularly propylene, require stabilization against thermal degradation to prevent significant changes in the properties of the polymeric material during melt processing. For example, without adequate stabilization, the melt-flow rate of polypropylene changes significantly during its extrusion in the compounding of various formulations and products. Various cyclic phosphites and the use thereof in polyolefins are well-known. See, for example, U.S. Pat. Nos. 3,441,633, 3,467,733, 3,592,858, 3,714,302, 4,252,750 and 4,673,701. The novel cyclic phosphites provided by our invention are non-volatile and are effective process stabilizers for polymeric materials.

The cyclic phosphites of this invention have the general formula

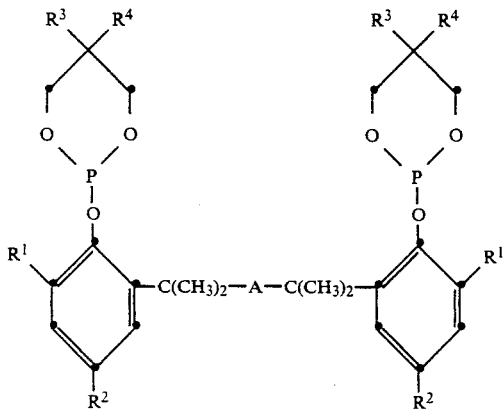

wherein
each $R^1$ is independently selected from hydrogen, alkyl, aralkyl, aryl, carboxy, alkoxycarbonyl or halogen;
each $R^2$ is independently selected from hydrogen, alkyl, aralkyl, alkoxy, aryl, carboxy, alkoxycarbonyl or halogen;
each $R^3$ and $R^4$ is alkyl; and
A is 1,3- or 1,4-phenylene.

Examples of the alkyl groups represented by $R^1$, $R^2$, $R^3$ and $R^4$ include alkyl containing up to about 18 carbon atoms such as methyl, ethyl, propyl, 2-propyl, butyl, 2-butyl, 2-methyl-2-propyl, pentyl, 2-pentyl, hexyl, 2-ethylhexyl, 2,4,4-trimethyl-2-pentyl, decyl, dodecyl, hexadecyl and octadecyl. The alkyl groups represented by $R^1$ and $R^2$ preferably contain up to 8 carbon atoms whereas the alkyl groups represented by $R^3$ and $R^4$ preferably contain up to about 4 carbon atoms, especially methyl. The alkoxy groups which $R^2$ can represent and the alkoxy moiety of the alkoxycarbonyl groups which $R^1$ and $R^2$ can represent may contain up to about 8 carbon atoms and include methoxy, ethoxy, propoxy, butoxy, hexyloxy, octyloxy and isomers thereof. The aryl groups represented by $R^1$ and $R^2$ and the aryl moieties of the aralkyl radicals represented by $R^1$ and $R^2$ may be unsubstituted phenyl or phenyl substituted with 1 or 2 groups selected from lower, i.e., containing up to about 4 carbon atoms, alkyl, lower alkoxy or halogen, e.g., chlorine or bromine. The alkyl moiety of the aralkyl groups typically is lower alkyl.

The compounds of formula (I) may be prepared by reacting a cyclic phosphite chloride having the formula

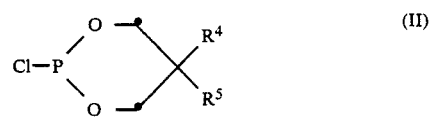

with a bis(hydroxyphenylpropyl)benzene compound having the structure

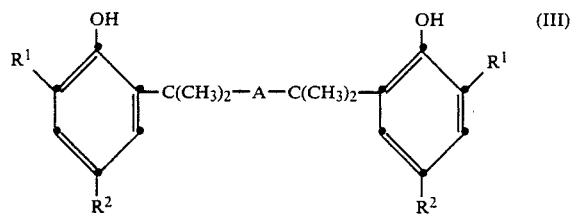

according to known procedures, where $R^1$, $R^2$, $R^3$ and $R^4$ are defined above. The cyclic phosphite chloride compounds of formula (II) may be prepared according to known procedures such as those described in the references cited hereinabove.

The bis(hydroxyphenylpropyl)benzene compounds of formula (II) are prepared by reacting m- or p-diisopropenylbenzene with phenols having the formula

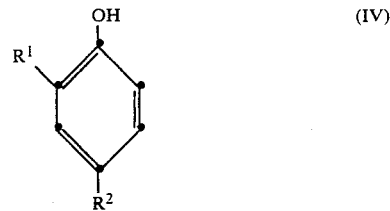

wherein $R^1$ and $R^2$ are defined above. Example of phenols (IV) include 2-methylphenol, 2,4-bis(2-methyl-2-butyl)phenol, 4-(2,4,4-trimethyl-2-pentyl)phenol, 2,4-bis(2-methyl-2-propyl)phenol, 4-methylphenol, 2-(2-methyl-2-propyl)-4-methylphenol, 4-octylphenol, 4-dodecylphenol, 2-(2-butyl)-4-(2-methyl-2-propyl)-phenol, 4-methoxyphenol, 4-chlorophenol, 4-methoxycarbonylphenol, 4-(2-phenyl-2-propyl)phenol and 2-methyl-4-(1-phenylethyl)phenol. Additional examples of phenols (IV) are given in U.S. Pat. Nos. 4,141,903, 4,219,480 and 4,275,004.

The compounds of our invention which are preferred are those of formula (I) wherein
$R^1$ is hydrogen or alkyl of up to about 8 carbon atoms;
$R^2$ is alkyl or alkoxy of up to about 8 carbon atoms, phenylalkyl of 7 to about 9 carbon atoms, chloro or methoxycarbonyl; and $R^3$ and $R^4$ each is methyl.

The cyclic phosphite compounds of our invention and their preparation are further illustrated by the following examples.

EXAMPLE 1

Phosphorus trichloride (171.7 g, 1.25 mol) is added dropwise over a period of 90 minutes to a slurry of neopentyl glycol (130 g, 1.25 mol) in 750 mL of toluene. The reaction mixture is stirred at 0° to 5° C. for an additional 4 hours.

To a portion of the above toluene solution containing 0.134 moles of 2-chloro-5,5-dimethyl-1,3,2-dioxaphosphorinane prepared as described above is added dropwise 1,3-bis-[2-[2-(2-hydroxy-5-methylphenyl)]propyl]-benzene (18.7 g, 0.05 moles) dissolved in pyridine (50 mL) over a period of 30 minutes. The reaction mixture is heated to and held at 80° C. for 3 hours. The resulting pyridine hydrochloride salt is removed by filtration and the toluene and excess pyridine are removed by distillation. The residue is dissolved in heptane and the bis-dioxaphosphorinane product having the structure

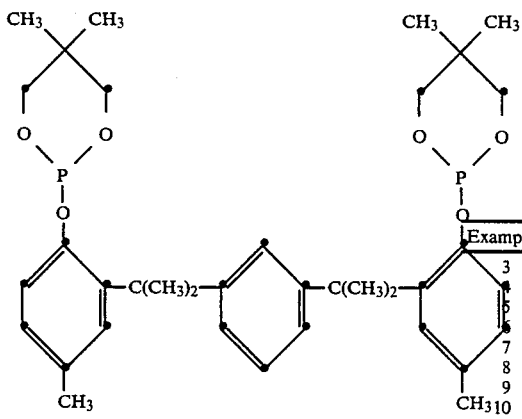

is crystallized from the heptane and collected by filtration to obtain 18.5 g of product (58% of theory). Molecular weight by Field Desorption Mass Spectrometry is 638.

EXAMPLE 2

The procedure described in the second paragraph of Example 1 is repeated using a portion of the toluene solution containing 0.028 moles of 2-chloro-5,5-dimethyl-1,3,2-dioxaphosphorinane prepared as described in Example 1 and 1,4-bis-[2-[2-(2-hydroxy-5-methylphenyl)]propyl]benzene (4.86 g, 0.013 moles) dissolved in pyridine (25 mL) over a period of 30 minutes. The reaction mixture is heated to and held at 28° C. overnight. The product having the structure

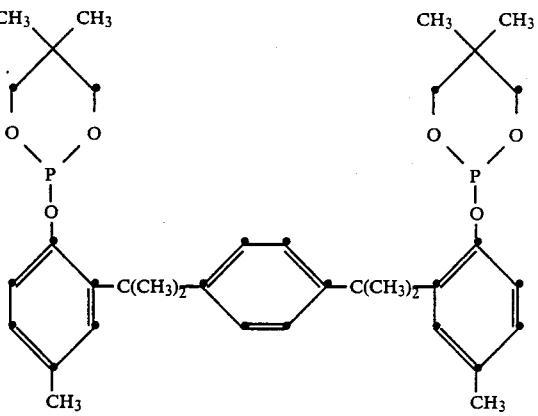

is recovered in a 70.5% yield by the procedure of Example 1. Molecular weight by FDMS is 638. Additional cyclic phosphite compounds provided by our invention are set forth in the Table I. These compounds conform to formula (I) wherein A is a phenylene radical, either 1,3- or 1,4- as indicated and may be prepared by the procedures described hereinabove by reacting the appropriate bis-(hydroxyphenylpropyl)benzene compound (III) with a cyclic phosphite chloride of formula (II).

TABLE I

| Example | $R^1$ | $R^2$ | $R^3$ | $R^4$ | A |
|---|---|---|---|---|---|
| 3 | H | —CH$_3$ | —C$_2$H$_5$ | —C$_2$H$_5$ | 1,3- |
| 4 | —CH$_3$ | —CH$_3$ | —CH$_3$ | —CH$_3$ | 1,3- |
| 5 | —C(CH$_3$)$_3$ | —CH$_3$ | —(CH$_2$)$_4$H | —C$_2$H$_5$ | 1,3- |
| 6 | —C(CH$_3$)$_3$ | —CH$_3$ | —(CH$_2$)$_4$H | —C$_2$H$_5$ | 1,4- |
| 7 | H | —C(CH$_3$)$_3$ | —CH$_3$ | —CH$_3$ | 1,3- |
| 8 | H | —C(CH$_3$)$_3$ | —CH$_3$ | —CH$_3$ | 1,4- |
| 9 | H | —C(CH$_3$)$_2$CH$_2$C(CH$_3$)$_3$ | —CH$_3$ | —CH$_3$ | 1,3- |
| 10 | H | —C(CH$_3$)$_2$CH$_2$C(CH$_3$)$_3$ | —CH$_3$ | —CH$_3$ | 1,4- |
| 11 | H | —CH$_3$ | —(CH$_2$)$_4$H | —C$_2$H$_5$ | 1,3- |
| 12 | H | —CH$_3$ | —(CH$_2$)$_4$H | —C$_2$H$_5$ | 1,3- |
| 13 | —C(CH$_3$)$_2$C$_6$H$_5$ | —C(CH$_3$)$_2$C$_6$H$_5$ | —CH$_3$ | —CH$_3$ | 1,3- |
| 14 | H | —COOCH$_3$ | —CH$_3$ | —CH$_3$ | 1,4- |
| 15 | H | Cl | —CH$_3$ | —CH$_3$ | 1,3- |
| 16 | —C(CH$_3$)$_3$ | —OCH$_3$ | —CH$_3$ | —CH$_3$ | 1,3- |

The bis-cyclic phosphite compounds of formula (I) may be used in a wide variety of synthetic polymeric materials which are susceptible to degradation upon exposure to heat and/or radiation including both visible and ultraviolet light. Examples of such polymeric materials include homo- and co-polymers of α-olefins such as polyethylene, polypropylene, polybutene, poly-3-methylbutene and ethylene-propylene copolymers, ethylene-vinyl acetate copolymers, polystyrene, copolymers of styrene with other ethylenically-unsaturated monomers such as maleic anhydride, butadiene and acrylonitrile, polyvinyl acetate, acrylonitrile-butadiene-styrene polymers, polymethacrylate polymers, polyvinyl formal, polyvinyl butyral, polyamides such as polycaprolactam (nylon 6), polycarbonates, unsaturated polyesters and polyvinylidene chloride. The preferred stabilized compositions of our invention comprise homo- and copolymers of α-olefins of 2 to 4 carbon atoms, especially polypropylene, containing a stabilizing amount of one or more of the compounds of formula (I).

The concentration of the bis-cyclic phosphite compounds in the polymeric material which will effectively inhibit polymer degradation can vary considerably depending on the particular polymer being stabilized and the end use for which the stabilized polymeric material is designed. Generally, concentration in the range of 0.001 to 5.0 weight percent may be used with concentrations of about 0.01 to 0.5 being most common. The bis-cyclic phosphite stabilizers provided by this invention typically will be used in combination with other conventional stabilizers such as phenolic antioxidants, polyvalent salts of organic acids and thioethers. In addition, other additives, such as plasticizers, lubricants, emulsifiers, antistatic agents, flame retardant agents, pigments and fillers, commonly used in formulating commercial polymeric compositions may be present.

The bis-cyclic phosphite stabilizer may be incorporated into the polymeric materials by conventional blending techniques. For example, the stabilizer may be added directly to a melt of the polymer on a roll mill to distribute the phosphite compound uniformly throughout the polymer. Alternatively, the bis-cyclic phosphite compound may be dry-blended with a finely-divided form of the polymer such as pellets and then the dry mix can be mixed further in and extruded from an extruder.

The utility of the bis-cyclic phosphite compounds as processing stabilizers for polyolefins is further illustrated by the following examples.

EXAMPLES 17 AND 18

Polypropylene, 0.05 phr (parts by weight per 100 parts by weight polypropylene) calcium stearate, 0.05 phr 2,2-bis[[3-[3,5-bis(1,1-dimethyl-ethyl)-4-hydroxyphenyl]-1-oxopropoxy]methyl]-1,3-propanediyl 3,5-bis(1,1-dimethylethyl)-4-hydroxy-benzenepropanoate (Irganox 1010 stabilizer) and (i) 0.05 phr of the biscyclic phosphite compound of Example 1 (Example 17), (ii) 0.05 phr of the bis-cyclic compound of Example 2 (Example 18) or no bis-cyclic compound (Control) are dry blended by shaking the additives and polypropylene pellets together in a plastic bag. Each of the polypropylene compositions then was melt blended in and extruded from a Brabender single screw rod extruder at 260° C. Each composition was extruded five times. After each extrusion, the melt-flow rate (ASTM Method D 1238, Procedure A, Condition E; g/10 minutes, MFR) was measured for each sample. The inhibiting effect of each phosphite compound on the thermal degradation of the polypropylene is shown in Table II.

TABLE II

| Number of Extrusions | Melt Flow Rate of Compositions | | |
|---|---|---|---|
| | Example 17 | Example 18 | Control |
| 1 | 3.6 | 3.7 | 5.6 |
| 2 | 4.1 | 4.3 | 7.1 |
| 3 | 4.8 | 4.9 | 8.9 |
| 4 | 5.5 | 5.6 | 9.8 |
| 5 | 6.3 | 6.4 | 11.3 |

The invention has been described in detail with particular reference to preferred embodiments thereof, but it will be understood that variations and modifications will be effected within the spirit and scope of the invention.

We claim:
1. A compound having the formula

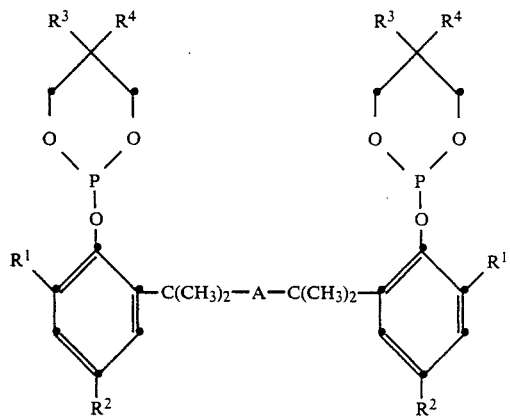

wherein
each $R^1$ is independently selected from hydrogen, alkyl, aralkyl, aryl, carboxy, alkoxycarbonyl or halogen;
each $R^2$ is independently selected from hydrogen, alkyl, aralkyl, alkoxy, aryl, carboxy, alkoxycarbonyl or halogen;
each $R^3$ and $R^4$ is alkyl; and
A is 1,3- or 1,4-phenylene.
2. A compound according to claim 1 wherein
$R^1$ is hydrogen or alkyl of up to about 8 carbon atoms;
$R^2$ is alkyl or alkoxy of up to about 8 carbon atoms, phenylalkyl of 7 to about 9 carbon atoms, chloro or methoxycarbonyl; and
$R^3$ and $R^4$ each is methyl.
3. A compound having the formula

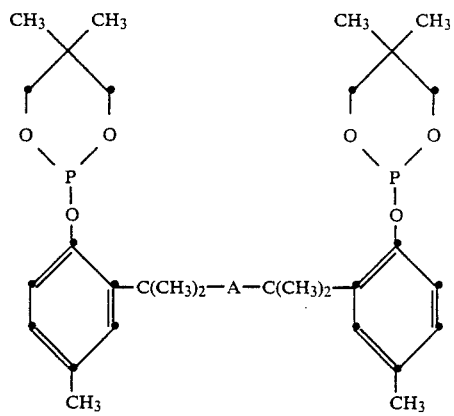

wherein A is 1,3- or 1,4-phenylene.
4. A stabilized composition comprising a synthetic polymeric material susceptible to degradation upon exposure to heat and/or radiation containing a stabilizing amount of a compound defined in claim 1.
5. A stabilized composition comprising a synthetic polymeric material susceptible to degradation upon exposure to heat and/or radiation containing a stabilizing amount of a compound defined in claim 2.
6. A stabilized composition comprising a synthetic polymeric material susceptible to degradation upon exposure to heat and/or radiation containing about 0.01 to 0.5 weight percent based on the weight of the polymeric material of a compound defined in claim 1.
7. A stabilized composition comprising a synthetic polymeric material susceptible to degradation upon exposure to heat and/or radiation containing about 0.01 to 0.5 weight percent based on the weight of the polymeric material of a compound defined in claim 2.

8. A stabilized composition comprising a synthetic polymeric material susceptible to degradation upon exposure to heat and/or radiation containing about 0.01 to 0.5 weight percent based on the weight of the polymeric material of a compound defined in claim 3.

9. A stabilized composition according to claim 4 wherein the polymeric material is an alpha-olefin homo- or co-polymer.

10. A stabilized composition according to claim 4 wherein the polymeric material is polypropylene.

11. A stabilized composition comprising an alpha-olefin homo- or co-polymer containing from about 0.01 to 0.05 weight percent based on the weight of the alpha-olefin polymer of a compound defined in claim 2.

12. A stabilized composition comprising an alpha-olefin homo- or co-polymer containing from about 0.01 to 0.05 weight percent based on the weight of the alpha-olefin polymer of a compound defined in claim 4.

* * * * *